US010376622B2

(12) United States Patent
Poirier (10) Patent No.: US 10,376,622 B2
(45) Date of Patent: Aug. 13, 2019

(54) PREVENTION OF AORTIC VALVE FUSION (71) Applicant: TC1 LLC, St. Paul, MN (US)

(72) Inventor: Victor Poirier, Concord, MA (US)

(73) Assignee: TC1 LLC, St. Paul, MN (US)

(*) Notice: Subject to any disclaimer, the term of this patent is extended or adjusted under 35 U.S.C. 154(b) by 0 days.

(21) Appl. No.: 16/034,129

(22) Filed: Jul. 12, 2018

(65) Prior Publication Data

US 2019/0001035 A1 Jan. 3, 2019

Related U.S. Application Data (60) Continuation of application No. 15/601,781, filed on May 22, 2017, now Pat. No. 10,046,098, which is a division of application No. 14/022,312, filed on Sep. 10, 2013, now Pat. No. 9,687,596, which is a continuation of application No. 12/394,185, filed on Feb. 27, 2009, now Pat. No. 8,562,507.

(51) Int. Cl.
A61M 1/10 (2006.01)
A61M 1/12 (2006.01)

(52) U.S. Cl.
CPC .......... *A61M 1/1086* (2013.01); *A61M 1/122* (2014.02); *A61M 1/101* (2013.01); *A61M 2205/3334* (2013.01); *A61M 2205/3344* (2013.01); *A61M 2205/3351* (2013.01); *A61M 2205/3355* (2013.01)

(58) Field of Classification Search
CPC .... A61M 1/101; A61M 1/1086; A61M 1/122; A61M 2205/3344; A61M 2205/3351; A61M 2205/3355
See application file for complete search history.

(56) References Cited

U.S. PATENT DOCUMENTS

| 3,240,207 | A | 3/1966 | Barker et al. |
| 3,911,897 | A | 10/1975 | Leachman |
| 4,190,057 | A | 2/1980 | Hill et al. |
| 4,600,855 | A | 7/1986 | Strachan |
| 4,957,504 | A | 9/1990 | Chardack |
| 5,139,517 | A | 8/1992 | Corral |
| 5,279,292 | A | 1/1994 | Baumann et al. |
| 5,289,821 | A | 3/1994 | Swartz |
| 5,318,592 | A | 6/1994 | Schaldach |

(Continued)

FOREIGN PATENT DOCUMENTS

| CA | 2533019 | 1/2005 |
| EP | 445782 | 8/1994 |

(Continued)

OTHER PUBLICATIONS

Bullister et al., "Physiologic Control Algorithms for Rotary Blood Pumps using Pressure Sensor Input", Organs, vol. 26, No. 11, 2002, pp. 931-938.

(Continued)

*Primary Examiner* — Amanda K Hulbert
(74) *Attorney, Agent, or Firm* — Kilpatrick Townsend and Stockton LLP (57) ABSTRACT Materials and methods related to blood pump systems are described. These can be used in patients to, for example, monitor arterial pressure, measure blood flow, maintain left ventricular pressure within a particular range, avoid left ventricular collapse, prevent fusion of the aortic valve in a subject having a blood pump, and provide a means to wean a patient from a blood pump.

17 Claims, 5 Drawing Sheets

(56) References Cited

U.S. PATENT DOCUMENTS

| | | |
|---|---|---|
| 5,385,581 A | 1/1995 | Bramm et al. |
| 5,503,615 A | 4/1996 | Goldstein |
| 5,658,318 A | 8/1997 | Stroetmann et al. |
| 5,693,091 A | 12/1997 | Larson et al. |
| 5,715,837 A | 2/1998 | Chen |
| 5,725,357 A | 3/1998 | Nakazeki et al. |
| 5,798,454 A | 8/1998 | Nakazeki et al. |
| 5,807,258 A | 9/1998 | Cimochowski et al. |
| 5,888,242 A | 3/1999 | Antaki et al. |
| 6,027,498 A | 2/2000 | Mutch et al. |
| 6,048,363 A | 4/2000 | Nagyszalanczy et al. |
| 6,053,873 A | 4/2000 | Govari et al. |
| 6,066,086 A | 5/2000 | Antaki et al. |
| 6,142,752 A | 11/2000 | Akamatsu et al. |
| 6,171,253 B1 | 1/2001 | Bullister et al. |
| 6,176,822 B1 | 1/2001 | Nix et al. |
| 6,264,601 B1 | 7/2001 | Jassawalla et al. |
| 6,277,078 B1 | 8/2001 | Porat et al. |
| 6,293,901 B1 | 9/2001 | Prem |
| 6,367,333 B1 | 4/2002 | Bullister et al. |
| 6,409,674 B1 | 6/2002 | Brockway et al. |
| 6,422,990 B1 | 7/2002 | Prem |
| 6,443,884 B1 | 9/2002 | Miyawaki |
| 6,481,292 B1 | 11/2002 | Reich |
| 6,540,658 B1 | 4/2003 | Fasciano et al. |
| 6,585,635 B1 | 7/2003 | Aldrich |
| 6,623,420 B2 | 9/2003 | Reich et al. |
| 6,636,769 B2 | 10/2003 | Govari et al. |
| 6,669,624 B2 | 12/2003 | Frazier |
| 6,716,189 B1 | 4/2004 | Jarvik et al. |
| 6,736,980 B2 | 5/2004 | Moscaritolo |
| 6,742,999 B1 | 6/2004 | Nüsser et al. |
| 6,890,303 B2 | 5/2005 | Fitz |
| 6,949,066 B2 | 9/2005 | Bearnson et al. |
| 6,974,436 B1 | 12/2005 | Aboul-Hosn et al. |
| 6,984,201 B2 | 1/2006 | Khaghani et al. |
| 6,991,595 B2 | 1/2006 | Burke et al. |
| 7,029,433 B2 | 4/2006 | Chang |
| 7,147,604 B1 | 12/2006 | Allen et al. |
| 7,160,242 B2 | 1/2007 | Yanai |
| 7,175,588 B2 | 2/2007 | Morello |
| 7,211,048 B1 | 5/2007 | Najafi et al. |
| 7,320,706 B2 | 1/2008 | Al-Najjar |
| 7,396,327 B2 | 7/2008 | Morello |
| 7,520,850 B2 | 4/2009 | Brockway |
| 7,645,225 B2 | 1/2010 | Medvedev et al. |
| 7,645,255 B2 | 1/2010 | Gordon et al. |
| 7,850,594 B2 | 12/2010 | Sutton et al. |
| 7,963,905 B2 | 6/2011 | Salmonsen et al. |
| 7,988,728 B2 | 8/2011 | Ayre |
| 7,998,054 B2 | 8/2011 | Bolling |
| 8,123,669 B2 | 2/2012 | Siess et al. |
| 8,246,530 B2 | 8/2012 | Sullivan |
| 8,562,507 B2 | 10/2013 | Poirier et al. |
| 8,657,733 B2 | 2/2014 | Ayre et al. |
| 8,771,165 B2 | 7/2014 | Choi et al. |
| 8,852,099 B2 | 10/2014 | Von Arx et al. |
| 9,387,284 B2 | 7/2016 | Heilman et al. |
| 9,433,714 B2 | 9/2016 | Voskoboynikov et al. |
| 9,687,596 B2 | 6/2017 | Poirier |
| 10,046,098 B2 | 8/2018 | Poirier |
| 2002/0183628 A1 | 12/2002 | Reich et al. |
| 2003/0023255 A1 | 1/2003 | Miles et al. |
| 2003/0045772 A1 | 3/2003 | Reich et al. |
| 2003/0074144 A1 | 4/2003 | Freed et al. |
| 2003/0199727 A1 | 10/2003 | Burke et al. |
| 2004/0034272 A1 | 2/2004 | Diaz et al. |
| 2005/0071001 A1 | 3/2005 | Jarvik |
| 2005/0107658 A1 | 5/2005 | Brockway |
| 2005/0159639 A1 | 7/2005 | Skliar et al. |
| 2006/0047205 A1 | 3/2006 | Ludomirsky et al. |
| 2006/0155158 A1 | 7/2006 | Aboul-Hosn |
| 2006/0229488 A1 | 10/2006 | Ayre et al. |
| 2006/0241335 A1 | 10/2006 | Benkowski et al. |
| 2007/0073393 A1 | 3/2007 | Kung et al. |
| 2007/0083077 A1 | 4/2007 | Frazier |
| 2007/0142923 A1 | 6/2007 | Ayre et al. |
| 2007/0282210 A1 | 12/2007 | Stern |
| 2008/0154095 A1 | 6/2008 | Stubkjaer et al. |
| 2008/0281146 A1 | 11/2008 | Morello |
| 2008/0319544 A1 | 12/2008 | Yaegashi |
| 2009/0099406 A1 | 4/2009 | Salmonsen et al. |
| 2009/0138080 A1 | 5/2009 | Siess et al. |
| 2009/0156885 A1 | 6/2009 | Morello et al. |
| 2010/0222632 A1 | 9/2010 | Poirier |
| 2010/0222633 A1 | 9/2010 | Poirier |
| 2010/0222634 A1 | 9/2010 | Poirier |
| 2010/0222635 A1 | 9/2010 | Poirier |
| 2010/0222878 A1 | 9/2010 | Poirier |
| 2014/0012067 A1 | 1/2014 | Poirier |
| 2014/0058190 A1 | 2/2014 | Gohean et al. |
| 2014/0275727 A1 | 9/2014 | Bonde et al. |
| 2015/0057488 A1 | 2/2015 | Yomtov |
| 2015/0151032 A1 | 6/2015 | Voskoboynikov et al. |
| 2015/0174307 A1 | 6/2015 | Eckman et al. |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0263299 A1 | 9/2016 | Xu et al. |
| 2017/0258974 A1 | 9/2017 | Poirier |

FOREIGN PATENT DOCUMENTS

| | | |
|---|---|---|
| EP | 499939 | 8/1994 |
| EP | 1046403 | 10/2000 |
| EP | 1354606 | 10/2003 |
| JP | 58054929 | 4/1983 |
| JP | 06011310 | 2/1994 |
| JP | 2002224066 | 8/2002 |
| JP | 2006528006 | 12/2006 |
| WO | 9215239 | 9/1992 |
| WO | 9959652 | 11/1999 |
| WO | 0069490 | 11/2000 |
| WO | 0112070 | 2/2001 |
| WO | 0172352 | 10/2001 |
| WO | 03015609 | 2/2003 |
| WO | 2004028593 | 4/2004 |
| WO | 2005006975 | 1/2005 |
| WO | 2005051838 | 6/2005 |
| WO | 2006133409 | 12/2006 |

OTHER PUBLICATIONS

Ednick et al., "Telemetric Recording of Intrapleural Pressure", Journal of Surgical Research, vol. 138, No. 1, 2007, pp. 10-14.

Ellozy et al., "First Experience in Human Beings with a Permanently Implantable Intrasac Pressure Transducer for Monitoring Endovascular Repair of Abdominal Aortic Aneurysms", J Vasc Surg., vol. 40, Sep. 2004, pp. 405-412.

Ferreira et al., "A Rule-Based Controller Based on Suction Detection for Rotary Blood Pumps", Conf Proc IEEE Eng Med Bioi Soc., 2007, pp. 3978-3981.

Giridharan et al., "Control Strategy for Maintaining Physiological Perfusion with Rotary Blood Pumps", Artif Organs, vol. 27, No. 7, 2003, pp. 639-648.

Haj-Yahia , "Midterm Experience with the Jarvik 2000 Axial Flow Left Ventricular Assist Device", J Thorac Cardiovasc Surg., vol. 134, No. 1, 2007, pp. 199-203.

Letsou et al., "Is Native Aortic Valve Commissural Fusion in Patients with Long-Term Left Ventricular Assist Devices Associated with Clinically Important Aortic Insufficiency", The Journal of Heart and Lung Transplantation, vol. 25, No. 4, Apr. 2006, pp. 395-399.

Ohuchi et al., "Control Strategy for Rotary Blood Pumps", Artif Organs, vol. 25, No. 5, May 2001, pp. 366-370.

Pittman et al., "Arterial and Central Venous Pressure Monitoring", International Anesthesiology Clinics, vol. 42, No. 1, 2004, pp. 13-30.

(56) References Cited

OTHER PUBLICATIONS

Reesink et al., "Suction Due to Left Ventricular Assist: Implications for Device Control and Management", Artif Organs, vol. 31, No. 7, 2007, pp. 542-549.
Rozenman, "Wireless Acoustic Communication with a Miniature Pressure Sensor in the Pulmonary Artery for Disease Surveillance and Therapy of Patients with Congestive Heart Failure", Journal of the American College of Cardiology, vol. 49, No. 7, Feb. 20, 2007, pp. 784-789.
Tuzun et al., "The Effect of Intermittent Low Speed Mode upon Aortic Valve Opening in Calves Supported with a Jarvik 2000 Axial Flow Device.", ASAIO Journal, vol. 51, No. 2, 2005, pp. 139-143.
Voigt et al., "Suction Detection for the Micromed Debakey Left Ventricular Assist Device", ASAIO Journal, vol. 51, No. 4, 2005, pp. 321-328.
Vollkron et al., "Development of a Reliable Automatic Speed Control System for Rotary Blood Pumps", The Journal of Heart and Lung Transplantation, vol. 24, No. 11, Nov. 2005, pp. 1878-1885.
Vollkron et al., "Development of a Suction Detection System for Axial Blood Pumps", Artif Organs, vol. 28, No. 8, 2004, pp. 709-716.

PREVENTION OF AORTIC VALVE FUSION

CROSS-REFERENCES TO RELATED APPLICATIONS

This application is a continuation of U.S. application Ser. No. 15/601,781 filed May 22, 2017, which is a divisional of U.S. application Ser. No. 14/022,312 filed Sep. 10, 2013, now U.S. Pat. No. 9,687,596 issued Jun. 27, 2017; which is a continuation of U.S. application Ser. No. 12/394,185 filed Feb. 27, 2009, now U.S. Pat. No. 8,562,507 issued Oct. 22, 2013, the entire contents of which are incorporated herein by reference in their entirety for all purposes.

TECHNICAL FIELD

This document relates to blood pumps, and more particularly to materials and methods for adjusting the speed of a blood pump based on information regarding the left ventricular and/or arterial pressure such that fusion of the aortic valve is avoided.

BACKGROUND

Blood pumps can be used to provide mechanical assistance to the heart. The left ventricle pushes blood out of the heart, through the aorta, and into the body, while the right ventricle pushes blood from the body to the lungs. Since the left ventricle bears the majority of the heart's load, it often is the first part of the heart to require assistance. Ventricular assistance can be provided by, for example, a pump that is implanted in the abdomen in parallel with the cardiovascular system. In many cases, an inflow conduit is attached to the left ventricle, and an outflow conduit is attached to the aorta. While some blood can follow its normal route out of the ventricle and into the aorta, other blood can pass through the pump, receive a boost, and be pushed into the body via the aorta.

BRIEF SUMMARY

The motor speed of a rotary blood pump can directly affect the level of assistance provided by the pump, and typically requires careful control. Blood pumps generally can respond to changes in demand for blood, so that when a subject exercises, for example, the speed of the pump can be made to increase to ensure that the heart provides adequate blood to the body. The speed of a blood pump may require balance, however. For example, a pump should not run so slowly that blood does not leave the heart, nor run so quickly that it causes suction in the ventricle, which can lead to ventricle collapse. Rotary pumps typically are most effective when they run at the upper end of their range, however.

This document is based in part on the development of blood pumps having one or more sensors positioned on or within the inflow conduit, the outflow conduit, or both. Such sensors can be used to assess left ventricular blood pressure and/or arterial blood pressure. As described herein, blood pressure sensed at an inflow conduit can be an approximation of left ventricular pressure, and blood pressure sensed at an outflow conduit can be an approximation of arterial pressure. The speed of a blood pump can be adjusted based on information regarding the left ventricular and/or arterial pressure such that, for example, left ventricular pressure is maintained at a level that averts ventricular collapse, weaning of a patient from the pump is facilitated, and fusion of the aortic valve is avoided. In addition, sensors placed at inflow and/or outflow conduits can be used for continuous, periodic, or on demand monitoring of blood flow and chronic measurement of arterial pressure.

A rotary blood pump produces constant flow, not pulsatile flow. With the absence or reduction of biologic pulsatile heart function, the patient's blood flow will convert from a pulsatile to a constant flow. The patient will not have a pulse, making standard blood pressure monitoring devices useless. A pump with a pressure transducer mounted on the outflow conduit provides an accurate determination of the arterial pressure on a continual or intermittent basis. Establishing accurate arterial measurements and transferring that information to an attending physician, for example, can greatly simplify patient management and pump operation.

In one aspect, this document features a blood pump system comprising a blood pump having an inflow conduit for receiving blood from a left ventricle of a heart and an outflow conduit for returning blood to a circulatory system, and a controller operably connected to the blood pump, wherein the inflow conduit comprises a first sensor located to detect an inflow conduit pressure that is substantially the same as left ventricular pressure, wherein the sensor is adapted to send a signal regarding the inflow conduit pressure to the controller, wherein the outflow conduit comprises a second sensor located to detect an outflow conduit pressure that is substantially the same as arterial pressure, wherein the sensor is adapted to send a signal regarding the outflow conduit pressure to the controller, and wherein the controller is adapted to send a signal to the blood pump such that the speed of the blood pump is periodically and transiently adjusted to increase left ventricular pressure relative to arterial pressure. The blood pump can comprise a motor that moves blood through the blood pump. Adjusting the speed of the motor can adjust the speed of the blood pump.

In another aspect, this document features a method for preventing aortic valve fusion in a subject having a blood pump system that bypasses the subject's aortic valve, the blood pump system comprising a blood pump, wherein the method comprises detecting left ventricular pressure via a sensor present at an inflow conduit of the blood pump system, detecting arterial pressure via a sensor present at an outflow conduit of the blood pump system, and periodically and transiently adjusting the speed of the blood pump such that the left ventricular pressure is increased sufficiently to permit the aortic valve to open. The blood pump can comprise a motor, wherein adjusting the speed of the motor can adjust the speed of the blood pump. The periodic and transient blood pump speed adjustment can be held constant for 5 to 10 beats. The periodic and transient blood pump speed adjustment can permit washing of the aortic valve sinus. The method can further comprise increasing the speed of the blood pump such that left ventricular pressure is reduced to a previous level.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
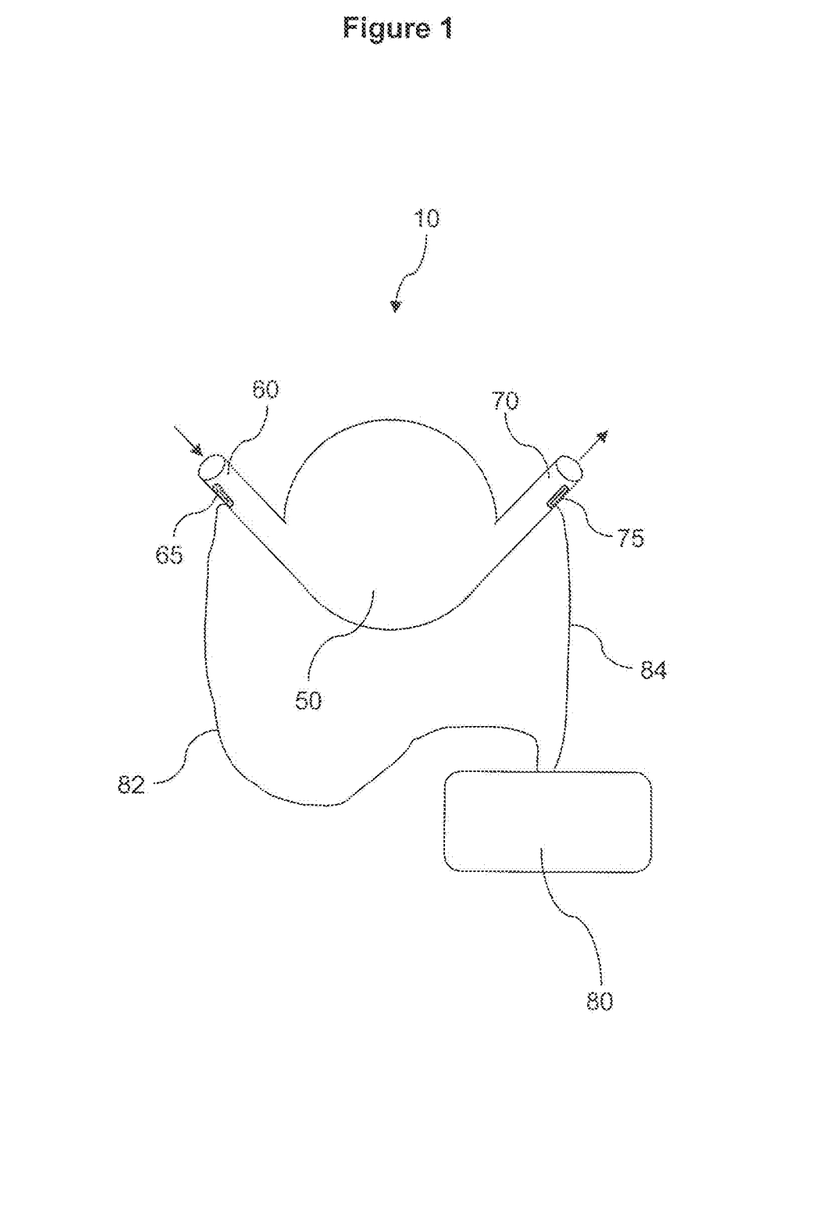
FIG. 1 is a depiction of an embodiment of a blood pump system as described herein.

This document provides materials and methods related to regulating the speed of a blood pump implanted in an individual, as well as materials and methods for chronically monitoring pressure and/or blood flow in a subject having an implanted blood pump. As depicted in FIG. 1, blood pump 10 as described herein can include pump housing 50, inflow conduit 60, and outflow conduit 70. Inflow conduit 60 can be configured to receive blood from the heart of a patient (e.g., from the left ventricle for a pump providing support for the systemic circulation, or from the right ventricle for a pump providing support to the pulmonary circulation), while outflow conduit 70 can be configured to return blood to the circulatory system of the patient (e.g., via the aorta for a pump providing support for the systemic circulation, or via the pulmonary artery for a pump providing support for the pulmonary circulation). In addition, either inflow conduit 60, outflow conduit 70, or both inflow conduit 60 and outflow conduit 70 can have one or more sensors that can be configured to measure blood pressure and/or blood flow. In some embodiments, as shown in FIG. 1, for example, sensor 65 can be positioned on an interior surface of inflow conduit 60, and sensor 75 can be positioned on an interior surface of outflow conduit 70. Sensors 65 and 75 can be located at any suitable position on conduits 60 and 70 (e.g., proximal to pump housing 50 or, as shown in FIG. 1, distal to pump housing 50). In some embodiments, a sensor can be within about 1 to about 2 cm (e.g., within about 0.75, about 1, about 1.25, about 1.5, about 1.75, about 2, or about 2.25 cm) from pump housing 50 and, for example, prior to any flexible member of blood pump 10. In some cases, a sensor can be positioned on the exterior surface of an inflow or outflow conduit (e.g., a flexible inflow or outflow conduit). A sensor can be, for example, a microelectromechanical system (MEMS), or a MEMS type transducer.

Blood pump 10 can be connected to a subject's circulatory system such that blood can flow from the subject's heart (e.g., from the left ventricle), through blood pump 10 via inflow conduit 60 and outflow conduit 70, and back into the subject's circulation (e.g., via the aorta). In some embodiments, sensor 65 can measure blood pressure at inflow conduit 60. Depending on the placement of sensor 65 on inflow conduit 60 (e.g., proximal or distal to pump housing 50), the pressure measured at inflow conduit 60 can be an approximation of the blood pressure within the subject's heart (e.g., can approximate left ventricular pressure if the pump is connected to the left ventricle). Sensor 75 can measure blood pressure at outflow conduit 70. Depending on the placement of sensor 75 on outflow conduit 70 (e.g., proximal or distal to pump housing 50), the pressure measured at outflow conduit 70 can be an approximation of arterial pressure.

Sensors 65 and 75 can serve a variety of purposes. Information regarding blood pressure and/or blood flow measured by sensor(s) on a blood pump can be sent to controller 80, which can be connected to the sensor(s) (e.g., via one or more leads, such as leads 82 and 84) or, as in other embodiments, via a wireless configuration and electrically transmitted. In some embodiments, a controller can chronically monitor detected blood pressure. For example, a sensor positioned on an outflow conduit can constantly, periodically, or on demand send information regarding detected blood pressure to a controller, allowing for chronic monitoring of arterial pressure since, as mentioned above, blood pressure measured at an outflow conduit can be an approximation of arterial pressure. In some embodiments, one or more sensors positioned at an inflow conduit, an outflow conduit, or both can send information regarding detected pressure to a controller (e.g., via one or more leads, or via wireless transmission). The controller, in turn, can send a signal to the pump such that the speed of the pump is adjusted (e.g., increased or decreased) depending on the blood pressure at the inflow conduit, the outflow conduit, or both. Such embodiments can allow for controlled weaning from the pump, maintain left ventricular pressure within a desired range, avoid left ventricular collapse, determine blood pump flow, and prevent aortic valve fusion, for example.

Systems having at Least a Sensor at an Inflow Conduit

In some embodiments, a blood pump system as described herein can be controlled based on information regarding blood pressure or blood flow at an inflow conduit. For example, a blood pump system can include a blood pump having an inflow conduit for receiving blood from a heart (e.g., from the left or right ventricle of a heart) and an outflow conduit for returning blood to the aorta or to the pulmonary circulation, and a controller operably connected to the blood pump. The inflow conduit can have a sensor to detect a conduit pressure, which may be substantially the same as left ventricular pressure if the inflow conduit receives blood from the left ventricle, or which may be substantially the same as right ventricular pressure if the inflow conduit receives blood from the right ventricle. The sensor can be adapted to send a signal regarding the conduit pressure to the controller. If the detected conduit pressure is less than a lower threshold level, for example, the controller can send a signal to the blood pump such that the speed of the pump is reduced. The lower threshold pressure level can be, for example, about 10 mm Hg to about 100 mm Hg (e.g., about 10 mm Hg, about 15 mm Hg, about 20 mm Hg, about 25 mm Hg, about 30 mm Hg, about 35 mm Hg, about 40 mm Hg, about 45 mm Hg, about 50 mm Hg, about 55 mm Hg, about 60 mm Hg, about 65 mm Hg, about 70 mm Hg, about 75 mm Hg, about 80 mm Hg, about 85 mm Hg, about 90 mm Hg, about 95 mm Hg, or about 100 mm Hg), or any value there between. In some cases, if the detected conduit pressure is greater than an upper threshold level, the controller can send a signal to the blood pump such that the speed of the pump is increased. The upper threshold pressure level can be, for example, about 10 mm Hg to about 45 mm Hg greater than the lower threshold pressure. In some cases, the upper threshold pressure can be about 55 mm Hg to about 150 mm Hg (e.g., about 55 mm Hg, about 60 mm Hg, about 65 mm Hg, about 70 mm Hg, about 75 mm Hg, about 80 mm Hg, about 85 mm Hg, about 90 mm Hg, about 95 mm Hg, about 100 mm Hg, about 110 mm Hg, about 120 mm Hg, about 130 mm Hg, about 140 mm Hg, or about 150 mm Hg), or any value there between. The controller can be adjusted by a clinician to set the threshold levels, and the threshold levels also can be changed as desired.

Figure 2:
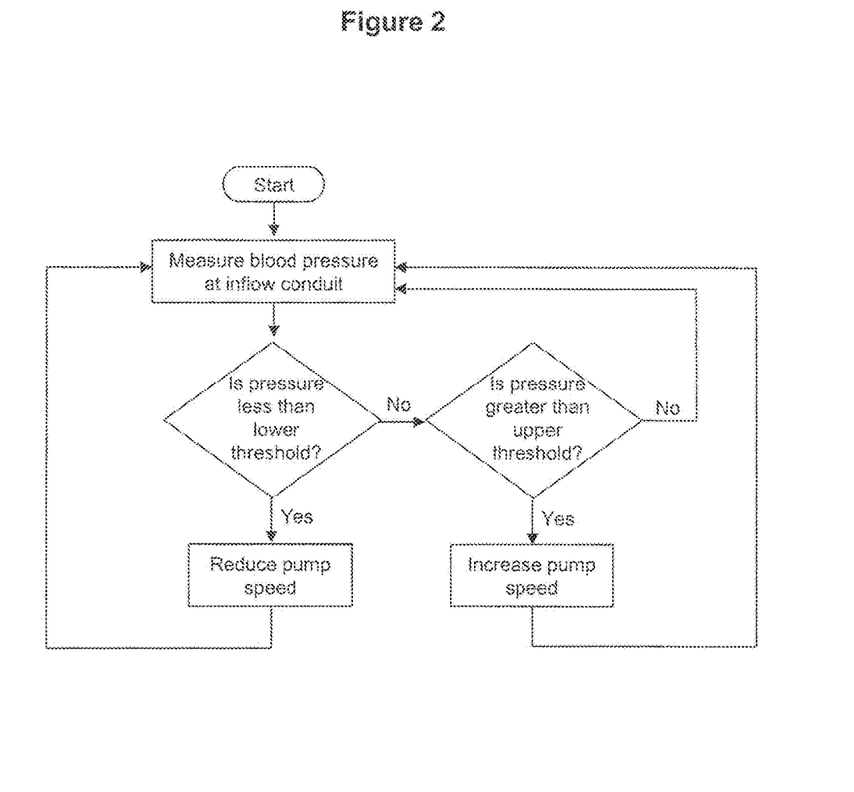
FIG. 2 is a flow diagram depicting an embodiment of a method for maintaining left ventricular pressure within a particular range.

Such a blood pump system can be useful to, for example, maintain left ventricular pressure within a preselected range while eliminating or avoiding left ventricular collapse. For example, a method can include detecting left ventricular pressure in a subject having a blood pump system, via a sensor at an inflow conduit of the blood pump, and increasing, maintaining, or reducing the speed of the blood pump based on the detected inflow conduit pressure. In order to maintain left ventricular pressure within a particular range, the speed can be reduced if the detected left ventricular pressure is less than a lower threshold level (thus increasing the left ventricular pressure), and the speed can be increased if the detected left ventricular pressure is greater than an upper threshold level (thus decreasing the left ventricular pressure). In this manner, left ventricular pressure can be maintained between the selected upper and lower thresholds. A flow diagram depicting such a method is shown in FIG. 2. Again, a clinician can set the upper and lower threshold values, depending on the patient, and can program the blood pump system accordingly. By maintaining the left ventricular pressure above a particular level (e.g., a lower threshold), one can prevent the pressure within the left ventricle from becoming negative, thus avoiding left ventricular collapse.

Similarly, a blood pump system can be useful to maintain right ventricular pressure within a preselected range. For example, a blood pump system for support of the pulmonary circulation can be configured such that the speed of the pump is continually monitored and adjusted (e.g., increased, decreased, or maintained) based on the right ventricular pressure detected via an inflow conduit sensor, such that a positive right ventricular pressure is maintained. To maintain right ventricular pressure within a particular range (e.g., from about 5 mm Hg to about 20 mm Hg), the speed of the pump can be reduced if the detected right ventricular pressure is less than a lower threshold level (thus increasing the right ventricular pressure), and the speed can be increased if the detected right ventricular pressure is greater than an upper threshold level (thus decreasing the right ventricular pressure). Again, a clinician can set the upper and lower threshold values, depending on the patient, and can program the blood pump system accordingly.

Figure 3:
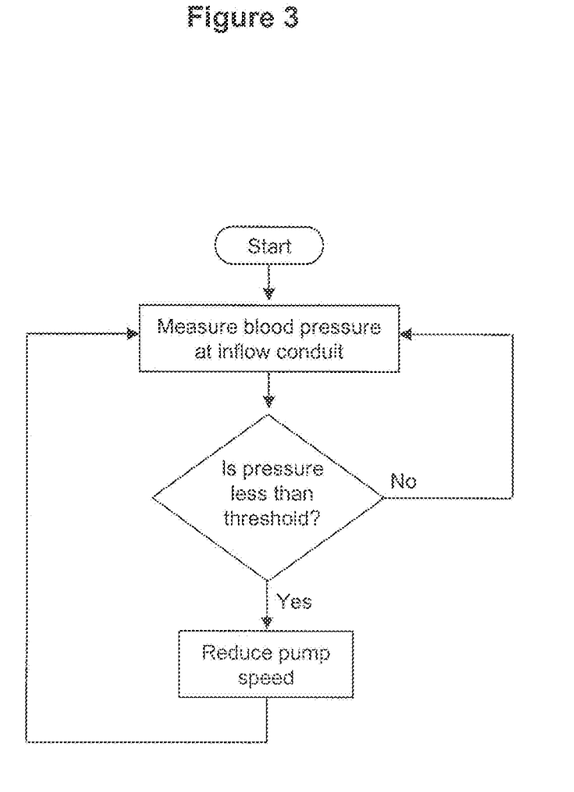
FIG. 3 is a flow diagram depicting an embodiment of a method for maintaining left ventricular pressure above a threshold level.

In some embodiments, the speed of a blood pump can be adjusted based only on whether the pressure measured at the inflow conduit is less than a lower threshold (e.g., as depicted in the flow diagram shown in FIG. 3). In such embodiments, the speed of the pump can be reduced if the detected pressure is less than a particular threshold, and can be maintained or increased if the detected pressure is not less than the threshold.

Such a blood pump system also can be useful for controlling blood flow in a subject. For example, blood flow in the subject can be detected via the inflow and outflow conduit sensors. Flow can be determined by measuring the pressure drop across the pump relative to the pump speed. The speed of the pump can be increased, maintained, or reduced based on the detected blood flow. If the detected blood flow is less than a lower threshold level, for example, the controller can send a signal to the blood pump such that the speed of the pump is increased. The lower threshold pressure level can be, for example, about 1 lpm to about 8 lpm, or any value there between. In some cases, if the detected blood flow is greater than an upper threshold level, the controller can send a signal to the blood pump such that the speed of the pump is reduced or maintained. The upper threshold pressure level can be, for example, from about 2 lpm to about 10 lpm (e.g., about 5 lpm to about 10 lpm), or any value there between.

In some embodiments, a blood pump system can be configured to facilitate gradual weaning of a patient from the pump. For example, a blood pump system can include a blood pump with an inflow conduit for receiving blood from a heart (e.g., from the left ventricle of a heart or from the right ventricle of a heart) and an outflow conduit for returning blood to the circulatory system (e.g., to the aorta or to the pulmonary artery), and a controller operably connected to the blood pump via, for example, wires or via wireless transmissions. The inflow conduit can have a sensor that can detect inflow conduit pressure that can be substantially the same as left ventricular pressure or right ventricular pressure, depending whether the system is placed to provide support to the systemic circulation or to the pulmonary circulation. The sensor can send a signal regarding the inflow conduit pressure to the controller, and the controller can send a signal to the blood pump such that the speed of the pump is reduced or maintained if the conduit pressure is less than a lower threshold level, or increased or maintained if the conduit pressure is greater than an upper threshold level. Thus, a system providing support to the systemic circulation can be configured to continually adjust the speed of the blood pump such that a positive systolic left ventricular pressure is maintained, and/or left ventricular end diastolic pressure is maintained within acceptable levels.

For a system providing support to the systemic circulation, for example, the lower threshold level can be from about 10 mm Hg to about 40 mm Hg (e.g., about 10 mm Hg, about 15 mm Hg, about 20 mm Hg, about 25 mm Hg, about 30 mm Hg, about 35 mm Hg, or about 40 mm Hg), or any value there between, and the upper threshold level can be about 65 mm Hg to about arterial pressure (e.g., about 65 mm Hg, about 70 mm Hg, about 75 mm Hg, about 80 mm Hg, about 85 mm Hg, about 90 mm Hg, or about arterial pressure), or any value there between. For a system providing support to the pulmonary circulation, for example, the lower threshold level can be from about 5 mm Hg to about 20 mm Hg, or any value there between, and the upper threshold level can be from about 20 mm Hg to about 60 mm Hg, or any value there between.

In some embodiments, a blood pump system can include a first blood pump having a first inflow conduit for receiving blood from a left ventricle of a heart and a first outflow conduit for returning blood to a circulatory system, a second blood pump having a second inflow conduit for receiving blood from a right ventricle or right atrium of a heart and a second outflow conduit for returning blood to a pulmonary system; and a controller operably connected to the first and second blood pumps. The first inflow conduit can have a first inflow sensor located to detect a first conduit pressure that is substantially the same as left ventricular pressure, and the first inflow sensor can be adapted to send a signal regarding the first conduit pressure to the controller. The second inflow conduit can have a second inflow sensor located to detect a second conduit pressure that is substantially the same as right ventricular pressure or right atrial pressure, and the second inflow sensor can be adapted to send a signal regarding the second conduit pressure to the controller.

The controller, in turn, can send a signal to the first blood pump such that the speed of the first blood pump is reduced if the first conduit pressure is less than a first lower threshold level (e.g., a lower left ventricular systolic threshold level), or is maintained or increased if the first conduit pressure is greater than a first upper threshold level (e.g., an upper left ventricular systolic threshold level). The first lower threshold level can be, for example, from about 10 mm Hg to about 100 mm Hg (e.g., 10 mm Hg, 20 mm Hg, 30 mm Hg, 40 mm Hg, 50 mm Hg, 60 mm Hg, 70 mm Hg, 80 mm Hg, 90 mm Hg, or 100 mm Hg), or any value there between, and the first upper threshold level can be from about 20 mm Hg to about 150 mm Hg (e.g., 20 mm Hg, 30 mm Hg, 40 mm Hg, 50 mm Hg, 60 mm Hg, 70 mm Hg, 80 mm Hg, 90 mm Hg, 100 mm Hg, 110 mm Hg, 120 mm Hg, 130 mm Hg, 140 mm Hg, or 150 mm Hg), or any value there between. Such a system can be configured to continually adjust the speed of the first blood pump such that a positive left ventricular pressure is maintained (e.g., a systolic left ventricular pressure in the range of 5 mm Hg to 50 mm Hg, or 10 mm Hg to 40 mm Hg).

The controller also can send a signal to the second blood pump such that its speed is reduced if the second conduit pressure is less than a second lower threshold level (e.g., a lower right ventricular systolic threshold level), or is maintained or increased if the second conduit pressure is greater than a second upper threshold level (e.g., an upper right systolic threshold level). The second lower threshold level can be from about 5 mm Hg to about 20 mm Hg (e.g., 5 mm Hg, 10 mm Hg, 15 mm Hg, or 20 mm Hg), or any value there between, and the second upper threshold level can be from about 20 mm Hg to about 60 mm Hg (e.g., 20 mm Hg, 30 mm Hg, 40 mm Hg, 50 mm Hg, or 60 mm Hg), or any value there between.

Such a blood pump system can be useful to, for example, continuously adjust the speed of the blood pump in order to maintain systolic left ventricular pressure within a narrow range, and also to assist in weaning the subject off the system. As the heart of a subject with a blood pump becomes stronger, it will generate more of its own pressure. Decreasing pump speed as the subject's heart becomes stronger can maintain the subject's overall blood pressure, which results from pressure generated by the heart. In embodiments where the blood pump system is placed to provide support to the systemic circulation, the speed of the blood pump is determined not by blood flow, but rather by the changing pressure generated by the left ventricle itself. In embodiments where the blood pump system is placed to provide support to the pulmonary circulation, the speed of the blood pump is determined by the changing pressure generated by the right ventricle.

A method for using such a blood pump system can include detecting left or right ventricular pressure, or both left and right ventricular pressure, via one or more inflow conduit sensors, and increasing, maintaining, or decreasing the speed of the blood pump based on the detected ventricular pressure(s). For example, the pump speed can be increased if the detected inflow conduit pressure is greater than an upper threshold level, and decreased if the detected inflow conduit pressure is less than a lower threshold level. A clinician can set the upper and lower thresholds on the controller, and can adjust the thresholds as desired.

In some embodiments, if the measured inflow conduit pressure is within the selected range, a blood pump system as described herein can facilitate weaning by shutting down for a particular length of time or number of heart beats, for example, and then starting up again (e.g., to return to the previously set speed). Such systematic reduction in the amount of support that the system provides to a subject can allow for recovery of the subject's own heart, and can enable subsequent removal of the blood pump from the subject. For example, full cardiac support may be accomplished when the maximum amount of blood is pumped out of the left ventricle without left ventricular collapse. This can be achieved by maintaining a positive systolic pressure within the left ventricle in a relatively narrow range (e.g., about a 20 mm Hg range), selectable between 0 and arterial pressure, and by continuously adjusting the pump speed to maintain this pressure. Partial support can be obtained when systolic pressure within the left ventricle is maintained at about arterial pressure level throughout the systolic cardiac cycle. The speed of the pump can be reduced to accomplish this lower level of support.

Methods for weaning a patient from a blood pump can include a step-wise reduction of blood flow through the pump. The heart must rest, however, to allow recovery before it can fully take over the pumping function. This can be accomplished by gradually increasing the amount of time the biologic heart spends in partial support, while gradually decreasing the amount of time that the blood pump provides support. Initially, partial support by the biologic heart can be allowed for a short period of time (e.g., as selected by a clinician), after which the pump speed can be increased to provide full support for a second length of time. Such an alternating low flow, high flow cycle can be repeated any number of times and as often as desired, to ensure that arterial pressure does not decrease appreciably during the times at which the biologic heart provides partial support. This is important, as a drop in arterial pressure can indicate that the biologic heart is not capable of producing sufficient blood flow in response to biologic demand. If a drop in pressure occurs, the motor speed can be automatically increased to full flow status. If a drop in pressure does not occur, the length of time in the partial support period can be increased (e.g., incrementally), provided that arterial pressure remains stable. Partial support provided by the biologic heart for increasingly extended periods of time with adequate arterial pressure and low end diastolic pressure in the left ventricle can indicate cardiac recovery. In contrast, high end diastolic pressure can indicate cardiac failure.

Figure 4:
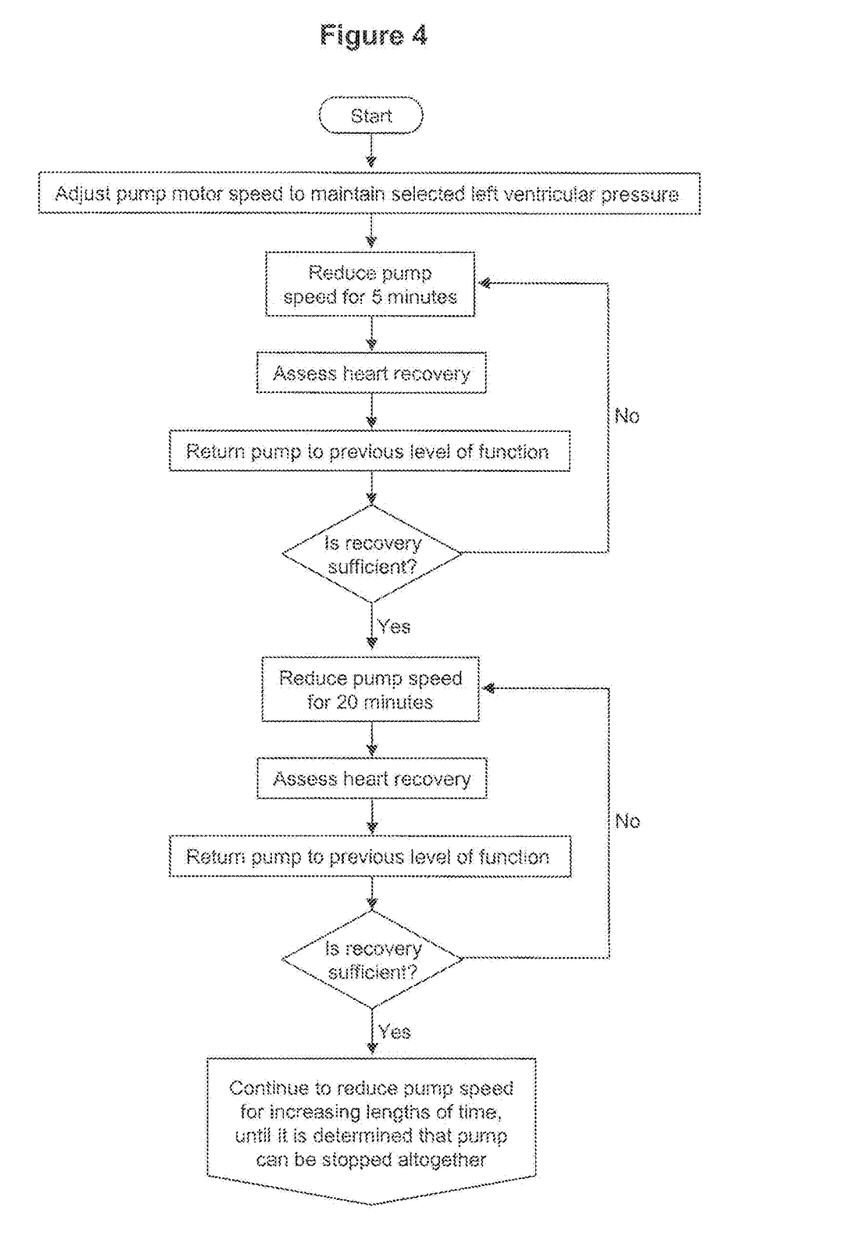
FIG. 4 is a flow diagram depicting an embodiment of a method for gradually weaning a subject off a blood pump system.

As indicated in FIG. 4, for example, an exemplary method for facilitating weaning of a subject from a blood pump can include the following steps:

(1) Adjust the pump motor speed to maintain a selected systolic left ventricular pressure between arterial pressure and about 20 mm Hg below arterial pressure for a desired number of beats or length of time (e.g., five minutes);

(2) greatly reduce the pump speed for a desired length of time (e.g., five minutes) and determine how well the heart recovers (e.g., based on inflow conduit pressure, which can approximate left ventricular pressure, such as left ventricular end diastolic pressure);

(3) return the pump to its previous level of function between arterial pressure and about 20 mm Hg less than arterial pressure;

(4) repeat steps (2) and (3) as desired;

(5) greatly reduce the pump speed for a longer length of time (e.g., 20 minutes) and determine how well the heart recovers;

(6) return the pump to its previous level of function between arterial pressure and about 20 mm Hg less than arterial pressure;

(7) repeat steps (5) and (6) as desired, at least until it is determined that arterial pressure does not decrease appreciably during step (5), and left ventricular end pressure is maintained at acceptable levels; and (8) continue as desired, gradually increasing the length of time for which the pump is turned down, until the subject can be weaned off the pump entirely. If the end diastolic pressure is above a threshold level (e.g., 20 mm Hg), the pump motor speed can be increased.

It is to be noted that the starting point for step (2) (e.g., the time for which the pump speed is initially reduced) can vary. For example, the blood pump initially can be slowed down for one to five minutes (e.g., for one, two, three, four, or five minutes), and that time then can be increased in subsequent cycles of the method. Appropriate starting points can be determined by a clinician, for example.

Another exemplary method for facilitating weaning of a subject from a blood pump providing support to the pulmonary circulation can include the following steps:

(1) adjusting the pump motor speed to maintain a selected right ventricular pressure between about 5 mm Hg and about 20 mm Hg;

(2) reducing the pump motor speed for a first selected number of beats and determining how well the heart recovers;

(3) returning the pump to its previous level of function;

(4) repeating steps (b) and (c) at least until the heart recovery is at an acceptable level;

(5) reducing the pump motor speed for a second selected number of beats that is incrementally greater than the first selected number of beats and determining how well the heart recovers;

(6) returning the pump to its previous level of function;

(7) repeating steps (5) and (6) at least until the heart recovery is at an acceptable level; and (8) gradually increasing the number of beats for which the pump motor speed is reduced, until the subject can be weaned off the blood pump system.

In some embodiments, blood flow measurements can be used as the control parameter, rather than pressure measurements. A blood pump can be operated at full support level, and blood pump flow can be established. Weaning then can be initiated by reducing the pump speed to reduce the flow by about 0.5 lpm to about 1.5 lpm (e.g., about 0.75 lpm, about 1 lpm, or about 1.5 lpm). Such a procedure can be carried out in steps, using time periods selected by a clinician, for example. Pump flow typically is not reduced to a level less than 1.0 lpm for long periods of time (e.g., 30 minutes). For a blood pump system providing support to the systemic circulation, arterial pressure can be monitored at each level to ascertain that it has not decreased appreciably or that the left ventricular end diastolic pressure has not risen appreciably. In the event that a pressure reduction does occur, the motor speed can be increased to a level at which arterial pressure can be maintained. For a blood pump system providing support to the pulmonary circulation, pulmonary artery pressure and/or central venous pressure (CVP) can be monitored at each level to ascertain that it has not decreased appreciably or that right ventricular pressure end diastolic pressure has not risen appreciably. If the end diastolic pressure or the CVP rises above a threshold level (e.g., 10 mm Hg to 20 mm Hg), the method can include increasing the pump motor speed.

Systems having at Least a Sensor at an Outflow Conduit

In some embodiments, a system as described herein can be used to provide data based on blood pressure and/or flow at an outflow conduit. For example, a blood pump system can be used for continuous, periodic, or on demand monitoring of arterial pressure (i.e., pressure of circulating blood on the arteries), or monitoring of pulmonary artery pressure, based on the pressure detected at an outflow conduit. In some cases, a blood pump system can include a blood pump having an inflow conduit for receiving blood from a heart (e.g., from the left ventricle or the right ventricle) and an outflow conduit for returning blood to a circulatory system (e.g., via the aorta) or to the pulmonary circulation, and a controller operably connected to the blood pump, where the outflow conduit has a sensor that can detect outflow conduit pressure. The outflow conduit pressure can be substantially the same as arterial pressure when the outflow conduit returns blood to the circulatory system via the aorta, for example, or can be substantially the same as pulmonary artery pressure when the outflow conduit returns blood to the pulmonary circulation.

The sensor can detect outflow conduit pressure on a continual basis or on a periodic basis (e.g., every second, every two seconds, every ten seconds, every 30 seconds, every minute, every two minutes, every five minutes, every 10 minutes, every hour, or less often). In some cases, the sensor can be configured to detect outflow conduit pressure on demand from a user or a clinician, for example. The sensor can be adapted to send a signal regarding the outflow conduit pressure to the controller and/or to a display. In some embodiments, the display can be part of the controller.

In some embodiments, the blood pump system can include an alarm adapted to activate if the conduit pressure drops below a preset level. Such a drop can be indicative of cardiac failure or pump failure. The alarm can provide any suitable type of signal to alert a user or a clinician of the pressure drop (e.g., an auditory signal, a visual signal, or a vibrational signal).

A blood pump system as provided herein can be used in methods for monitoring arterial or pulmonary artery pressure in a subject. For example, a method can include using a sensor located in an outflow conduit of a blood pump system to detect arterial pressure in a subject on a repeated basis, and outputting the detected arterial pressure for display. In another example, a method can include using a sensor located in an outflow conduit of a blood pump system to detect pulmonary artery pressure in a subject on a repeated basis, and outputting the detected pulmonary artery pressure for display. The sensor can detect conduit pressure on a continual basis or on a periodic basis (e.g., every second, every two seconds, every ten seconds, every 30 seconds, every minute, every two minutes, every five minutes, every 10 minutes, every hour, or less often), for example. In some cases, the sensor can be configured to detect outflow conduit pressure on demand from a subject (e.g., a user or a clinician).

A method also can include transmitting data regarding detected arterial or pulmonary artery pressure to a controller, where the controller can format the data for display. A controller also may process arterial or pulmonary artery pressure data to account for any difference between pressure in the outflow conduit and actual arterial or pulmonary artery pressure. For example, a controller can adjust conduit pressure by a adding or subtracting pre-determined amount. Further, in some cases, the detected (or calculated) arterial or pulmonary artery pressure can be displayed in response to an action from a user, e.g., via a controller or via a display operably connected to a controller.

Systems having Sensors at Both an Inflow Conduit and at an Outflow Conduit

In some embodiments, a blood pump system can be controlled based on information about blood pressure and/or blood flow at both an inflow conduit and an outflow conduit. For example, a blood pump system can include a blood pump having an inflow conduit for receiving blood from a heart (e.g., a left ventricle) and an outflow conduit for returning blood to a circulatory system (e.g., via the aorta), and a controller operably connected to the blood pump, wherein the inflow conduit has a first sensor for detecting an inflow conduit pressure that is substantially the same as left ventricular pressure, and wherein the outflow conduit has a second sensor for detecting an outflow conduit pressure that is substantially the same as arterial pressure. The first sensor can be adapted to send a signal regarding the inflow conduit pressure to the controller, and the second sensor can be adapted to send a signal regarding the outflow conduit pressure to the controller.

In some embodiments, the controller can be adapted to send a signal to the blood pump such that the speed of the blood pump (e.g., the speed of a motor in the blood pump) is periodically and transiently adjusted (e.g., reduced) so that left ventricular pressure increases. Such embodiments can be useful, for example, in subjects having blood pump systems that bypass the aortic valve, such that the aortic valve does not regularly open and close. Increasing left ventricular pressure by reducing pump speed (and thus reducing the flow of blood through the pump) can force the heart to pump blood through the aortic valve, thus forcing the aortic valve to open and reducing the likelihood that the valve will fuse shut while the pump is in use within the subject. It is noted that the left ventricular pressure does not necessarily need to exceed the arterial pressure in order for the aortic valve to open, since the valve typically can open if the left ventricular pressure is equal to the arterial pressure. In some cases, the speed of the pump only needs to be reduced such that left ventricular pressure and arterial pressure are substantially equal, although in some embodiments the speed can be reduced such that left ventricular pressure exceeds arterial pressure. Without being bound by a particular mechanism, left ventricular pressure can equal or exceed arterial pressure during systole, such that the aortic valve opens when the left ventricle contracts.

Figure 5:
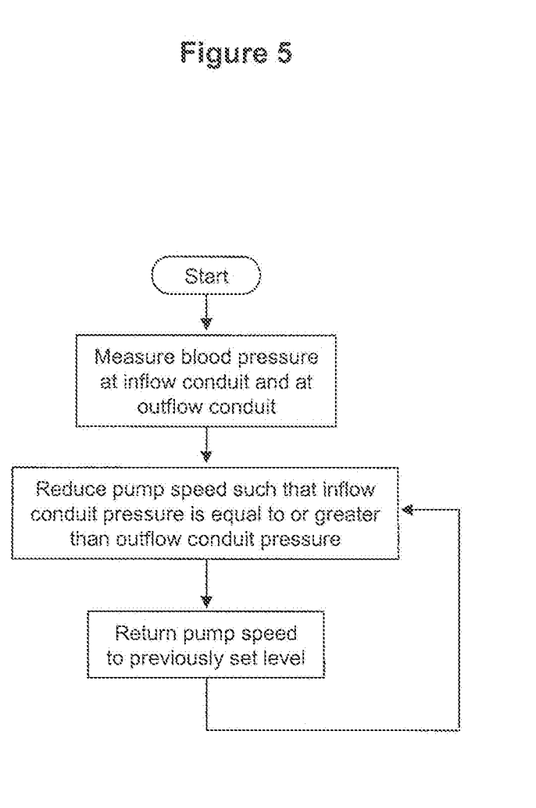
FIG. 5 is a flow diagram depicting an embodiment of a method for preventing aortic valve fusion in a subject having a blood pump system.

This document also provides a method for preventing aortic valve fusion in a subject having a blood pump as described herein. The method can include detecting left ventricular pressure via a sensor present at an inflow conduit of the blood pump, detecting arterial pressure via a sensor present at an outflow conduit of the blood pump, and periodically and transiently adjusting (e.g., reducing) the speed of the blood pump (e.g., via the blood pump motor) to such an extent that left ventricular pressure is increased relative to arterial pressure, thereby permitting the aortic valve to open. The pump speed can be adjusted based on time or based on heart beats, for example. For example, pump speed can be decreased for a particular length of time (e.g., 5 to 30 seconds) at particular intervals of time (e.g., every 5 to 20 minutes), or can be decreased for a particular number of heart beats (e.g., 5 to 30 beats) at particular intervals (e.g., every 300 to 1200 beats). In some cases, the reduced pump speed can occur over a length of time sufficient to permit washing of the aortic valve sinus. At the end of each cycle, the pump speed can be increased (e.g., to return to a previously set level), so that left ventricular pressure decreases relative to arterial pressure. A flow diagram showing an example of such a method is presented in FIG. 5.

In some embodiments, a blood pump system having sensors at both an inflow conduit and an outflow conduit can be used as a blood flow meter. Such systems can be used for continuous, periodic, or on demand monitoring of blood flow through the pump. A blood pump system can include, for example, a blood pump with an inflow conduit for receiving blood from the heart (e.g., from the left ventricle) and an outflow conduit for returning blood to the circulatory system (e.g., via the aorta), and a controller operably connected to the blood pump, wherein the inflow conduit has a first sensor for detecting an inflow conduit pressure and the outflow conduit has a second sensor for detecting an outflow conduit pressure. The inflow conduit pressure can be substantially the same as left ventricular pressure, and the first sensor can be adapted to send a signal regarding the inflow conduit pressure to the controller. Similarly, the outflow conduit pressure can be substantially the same as arterial pressure, and the sensor can be adapted to send a signal regarding the outflow conduit pressure to the controller. The controller, in turn, can be adapted to calculate blood flow through the pump based on the inflow conduit pressure and the outflow conduit pressure. Blood flow calculation can be based, for example, on blood pump motor speed and on pressure changes within the blood pump (e.g., the pressure drop across the pump). In some cases, the controller can be adapted to output information regarding calculated blood flow for display (e.g., on a continuous, periodic, or on-demand basis).

This document also provides a method for measuring blood flow through a blood pump in a subject. The method can include detecting left ventricular pressure via a sensor present at an inflow conduit of the blood pump, detecting arterial pressure via a sensor present at an outflow conduit of the blood pump, and calculating blood flow based on the difference between the left ventricular pressure and the arterial pressure. Thus, a blood flow calculation can be based on the pressure drop across the pump, as well as on motor speed. Information regarding blood flow can be output for display. Left ventricular and arterial pressures can be detected on a continuous, periodic, or on-demand basis. In addition, the method can include retrieving stored information regarding pressure changes within the blood pump.

Before such a blood pump is placed into the subject, it may be used in determining a constant for use in calculating the blood flow. For example, a technician can measure the flow rate across the pump to determine the pressure drop, and can derive a constant based on the particular configuration of the pump. The pump can be calibrated to determine the coefficient (multiplier) that can be used in calculation of blood flow after the blood pump has been connected to the subject and the pump system is in use. Blood pump flow can be calculated by the controller using the following equation:

Flow=(pump outlet pressure−pump inlet pressure)×C, where C=an empirically derived constant describing the pump geometry, surface conditions, and viscosity.

In some cases, flow can be determined by using a "look up table" of flow as a function of the pressure drop across the pump, in combination with motor speed.

Other Embodiments

It is to be understood that while the invention has been described in conjunction with the detailed description thereof, the foregoing description is intended to illustrate and not limit the scope of the invention, which is defined by the scope of the appended claims. For example, the blood pump may be a rotary pump, a centrifugal blood pump, or any other type of blood pump.

Additionally, a blood pump controller (e.g., controller 80) can be implanted or used externally in association with any of the computer-implemented methods described previously, according to one implementation. Controller 80 may include various forms of digital computers, such as microcontrollers, customized application-specific integrated circuits (ASICs), programmable logic controllers (PLCs), distributed control systems (DCSs), remote terminal units (RTUs), laptops, and any other appropriate computers.

A controller such as controller 80 can include, for example, a processor, a memory, a storage device, and an input/output device. Each of the components can be interconnected using a system bus. The processor can be capable of processing instructions for execution within the controller. The processor may be designed using any of a number of architectures. For example, the processor may be a CISC (Complex Instruction Set Computers) processor, a RISC (Reduced Instruction Set Computer) processor, or a MISC (Minimal Instruction Set Computer) processor.

In some embodiments, a processor can be a single-threaded processor. In some embodiments, a processor can be a multi-threaded processor. A processor can be capable of processing instructions stored in the memory or on a storage device to display graphical information for a user interface on an input/output device.

The memory can store information within controller 80. In some embodiments, the memory can be a computer-readable medium. In some cases, the memory can be a volatile memory unit. In other cases, the memory can be a non-volatile memory unit.

A storage device can be capable of providing mass storage for controller 80. In some embodiments, a storage device can be a computer-readable medium. In various cases, a storage device can be a hard disk device or an optical disk device.

An input/output device can provide input/output operations for controller 80. In some embodiments, an input/output device can include a display unit for displaying graphical user interfaces. The display may have a touch screen interface for receiving input from a user. Additionally, a input/output device can include buttons, dials, and/or switches on the controller for receiving information from a user.

The features described can be implemented in digital electronic circuitry, or in computer hardware, firmware, software, or in combinations thereof. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, and the sole processor or one of multiple processors of any kind of computer. Generally, a processor can receive instructions and data from a read-only memory or a random access memory, or both. The essential elements of a computer are a processor for executing instructions and one or more memories for storing instructions and data. A computer typically also will include, or be operatively coupled to communicate with, one or more mass storage devices for storing data files. Examples of such devices include magnetic disks, such as internal hard disks and removable disks magneto-optical disks, and optical disks. Storage devices suitable for tangibly embodying computer program instructions and data include all forms of non-volatile memory, including, by way of example, semiconductor memory devices (e.g., EPROM, EEPROM, and flash memory devices), magnetic disks such as internal hard disks and removable disks, and magneto-optical disks. The processor and the memory can be supplemented by, or incorporated in, ASICs.

To provide for interaction with a user, the features can be implemented on a computer having a display device such as a liquid crystal display (LCD) monitor for displaying information to the user.

It also is understood that while the invention described herein is of a blood pump to aid the left ventricle, other embodiments also are contemplated. For example, a blood pump with pressure transducers on the inlet and/or the outlet can be used to supplement flow from the right ventricle. The inlet conduit can be attached to the right atrium or the vena cava, which would indicate central venous pressure while the pump outlet conduit can be attached to the pulmonary artery (PA) to indicate PA pressure. In such embodiments, blood from the venous return can be pushed through the lungs to the left ventricle.

In some embodiments, one pump can be used on the right side and another pump can be used on the left side, thereby creating a total artificial heart or bilateral system. Total blood flow can be controlled by proper adjustment of the pressure levels at each pump. In some embodiments, the controller can be implanted in the patient with data transmission via a percutaneous lead, or with wireless transmission via an electrical signal.

Other aspects, advantages, and modifications are within the scope of the following claims.

What is claimed is:

1. A method of controlling a blood pump to facilitate gradual weaning of a patient from the blood pump, the blood pump receiving a flow of blood from a ventricle of the patient and outputting the flow of blood to an artery of the patient, the method comprising:
   controlling, by a controller, a speed of the blood pump over a first period of time encompassing multiple contractions of the ventricle to provide circulatory support to the patient to maintain a positive level of systolic blood pressure within the ventricle within a first predetermined range;
   subsequent to the first period of time, controlling, by the controller, the speed of the blood pump over a second period of time encompassing multiple contractions of the ventricle to provide a reduced level of circulatory support to the patient relative to the circulatory support provided to the patient over the first period of time;

subsequent to the second period of time, controlling, by the controller, the speed of the blood pump over a third period of time encompassing multiple contractions of the ventricle to provide circulatory support to the patient to maintain a positive level of systolic blood pressure within the ventricle within the first predetermined range; and determining, by the controller, whether the ventricle provided circulatory support to the patient over the second period of time that exceeded a predetermined minimum level of circulatory support.

2. The method of claim 1, wherein:
the ventricle is a left ventricle of the patient; and
the first predetermined range is between an aortic blood pressure of the patient and about 20 mm Hg below the aortic blood pressure.

3. The method of claim 1, wherein:
the ventricle is a right ventricle of the patient; and
the first predetermined range is between 5 mm Hg and 20 mm Hg.

4. The method of claim 1, wherein:
the blood pump is controlled to pump blood within a first predetermined range of flow rates to provide circulatory support to the patient over the first period of time;
the blood pump is controlled to pump blood at a reduced flow rate over the second period of time relative to the flow rate over the first period of time; and
the blood pump is controlled to pump blood within the first predetermined range of flow rates to provide circulatory support to the patient over the third period of time.

5. The method of claim 4, wherein the reduced flow rate is between about 0.5 liters/minute and 1.5 liters/minute less than a flow rate during the first period of time.

6. The method of claim 1, wherein the reduced level of circulatory support results in systolic blood pressure within the ventricle being maintained at about an arterial blood pressure within the artery.

7. The method of claim 1, wherein the first period of time is at least 5 minutes.

8. The method of claim 1, wherein the second period of time is between 1 and 5 minutes.

9. The method of claim 1, wherein:
the ventricle is a left ventricle of the patient;
the artery is an aorta of the patient; and
the method further comprises controlling, by the controller, the speed of the blood pump to revert from providing the reduced level of circulatory support to the patient to providing circulatory support to the patient to maintain a positive level of systolic blood pressure within the ventricle within the first predetermined range in response to detecting at least one of:
a decrease in aortic blood pressure of at least a first predetermined amount during the second period of time, and
an increase of an end diastolic blood pressure within the left ventricle of at least a second predetermined amount during the second period of time.

10. The method of claim 1, wherein:
the ventricle is a right ventricle of the patient;
the artery is a pulmonary artery of the patient; and
the method further comprises controlling, by the controller, the speed of the blood pump to revert from providing the reduced level of circulatory support to the patient to providing circulatory support to the patient to maintain a positive level of systolic blood pressure within the ventricle within the first predetermined range in response to detecting at least one of:
a decrease in pulmonary artery blood pressure of at least a first predetermined amount during the second period of time, and
an increase of an end diastolic blood pressure within the right ventricle of at least a second predetermined amount during the second period of time.

11. The method of claim 1, wherein the determination of whether the ventricle provided circulatory support to the patient over the second period of time that exceeded the predetermined minimum level of circulatory support comprises determining whether a decrease in blood pressure in the artery of at least a first predetermined amount occurs during the second period of time.

12. The method of claim 11, wherein the determination of whether the ventricle provided circulatory support to the patient over the second period of time that exceeded the predetermined minimum level of circulatory support comprises determining whether an increase of an end diastolic blood pressure within the ventricle of at least a second predetermined amount occurs during the second period of time.

13. The method of claim 1, further comprising:
in response to determining that the ventricle provided circulatory support to the patient over the second period of time that exceeded the predetermined minimum level of circulatory support,
subsequent to the third period of time, controlling, by the controller, the speed of the blood pump over a fourth period of time encompassing multiple contractions of the ventricle to provide a reduced level of circulatory support to the patient relative to the circulatory support provided to the patient over the third period of time, the fourth period of time being greater than the second period of time;
subsequent to the fourth period of time, controlling, by the controller, the speed of the blood pump over a fifth period of time encompassing multiple contractions of the ventricle to provide circulatory support to the patient to maintain a positive level of systolic blood pressure within the ventricle within the first predetermined range; and
determining, by the controller, whether the ventricle provided circulatory support to the patient over the fourth period of time that exceeded the predetermined minimum level of circulatory support.

14. The method of claim 3, further comprising:
in response to determining that the ventricle provided circulatory support to the patient over the fourth period of time that exceeded the predetermined minimum level of circulatory support,
subsequent to the fifth period of time, controlling, by the controller, the speed of the blood pump over a sixth period of time encompassing multiple contractions of the ventricle to provide a reduced level of circulatory support to the patient relative to the circulatory support provided to the patient over the fifth period of time, the sixth period of time being greater than the fourth period of time;
subsequent to the sixth period of time, controlling, by the controller, the speed of the blood pump over a seventh period of time encompassing multiple contractions of the ventricle to provide circulatory support to the patient to maintain a positive level of systolic blood pressure within the ventricle within the first predetermined range; and determining, by the controller, whether the ventricle provided circulatory support to the patient over the sixth period of time that exceeded the predetermined minimum level of circulatory support.

15. A method of controlling a blood pump to facilitate gradual weaning of a patient from the blood pump, the blood pump receiving a flow of blood from a ventricle of the patient and outputting the flow of blood to an artery of the patient, the method comprising:

receiving, by a controller, an input indicative of a blood pressure within the ventricle; and controlling, by the controller, a speed of the blood pump such that:

a blood pressure within the ventricle is maintained equal to or greater than a lower threshold for avoiding ventricular collapse, and the blood pressure within the ventricle is maintained equal to or less than an upper threshold to maintain an end diastolic blood pressure within an acceptable range.

16. The method of claim 15, wherein:

the ventricle is a left ventricle;

the lower threshold is within a range from 10 mm Hg to 40 mm Hg; and the upper threshold is within a range from 65 mm Hg to about a blood pressure within an aorta of the patient.

17. The method of claim 15, wherein:

the ventricle is a right ventricle;

the lower threshold within a range from 5 mm Hg to 20 mm Hg; and the upper threshold is within a range from 20 mm Hg to about 60 mm Hg.

* * * * *